United States Patent [19]
Jones

[11] Patent Number: 6,130,355
[45] Date of Patent: Oct. 10, 2000

[54] ANHYDROUS CARBONYLATION PROCESS FOR THE PRODUCTION OF ACETIC ACID

[75] Inventor: Michael David Jones, Yorkshire, United Kingdom

[73] Assignee: BP Chemicals Limited, London, United Kingdom

[21] Appl. No.: 09/220,355

[22] Filed: Dec. 24, 1998

[30] Foreign Application Priority Data

Jan. 31, 1998 [GB] United Kingdom .................. 9802027

[51] Int. Cl.$^7$ .................................................. C07C 51/10
[52] U.S. Cl. .......................................... 562/517; 562/519
[58] Field of Search ..................................... 562/517, 519

[56] References Cited

U.S. PATENT DOCUMENTS

| | | | |
|---|---|---|---|
| 4,046,807 | 9/1977 | Kuckertz | 260/549 |
| 4,690,912 | 9/1987 | Paulik et al. | |
| 4,792,620 | 12/1988 | Paulik et al. | |
| 5,003,104 | 3/1991 | Paulik et al. | |
| 5,281,751 | 1/1994 | Schreck | |
| 5,380,929 | 1/1995 | Erpenbach et al. | 562/519 |
| 5,831,120 | 11/1998 | Watson et al. | |
| 5,939,585 | 8/1999 | Ditzel et al. | 562/519 |

FOREIGN PATENT DOCUMENTS

| | | |
|---|---|---|
| 0097978 B1 | 1/1984 | European Pat. Off. |
| 0144935 A2 | 6/1985 | European Pat. Off. |
| 0144936 A2 | 6/1985 | European Pat. Off. |
| 0173170 B1 | 3/1986 | European Pat. Off. |
| 0 250 189 A1 | 12/1987 | European Pat. Off. |

*Primary Examiner*—Ardin H. Marschel
*Assistant Examiner*—Sherif Kafafi
*Attorney, Agent, or Firm*—Nixon & Vanderhye

[57] ABSTRACT

An anhydrous process for the production of acetic acid by the reaction of methanol, and/or dimethyl ether, with a gaseous reactant comprising carbon monoxide and hydrogen, the hydrogen being present in an amount less than 9 mole %, in the presence of a catalyst system comprising at least one noble metal of Group VIII of the Periodic Table as catalyst, a halo-compound as co-catalyst and an iodide salt as catalyst stabiliser which process comprises feeding methanol, and/or dimethyl ether, and gaseous reactant to a carbonylation reactor in which there is maintained a liquid reaction composition comprising: (i) methyl acetate in an amount from 1 to 35% w/w, (ii) acetic anhydride in an amount up to 8% w/w, (iii) halo-compound in an amount from 3 to 20% w/w, (iv) Group VIII noble metal catalyst in an amount from 1 to 2000 ppm, (v) sufficient iodide salt to provide from 0.5 to 20% by weight iodine as I$^-$ and (vi) acetic acid comprising the remainder of the composition.

24 Claims, 1 Drawing Sheet

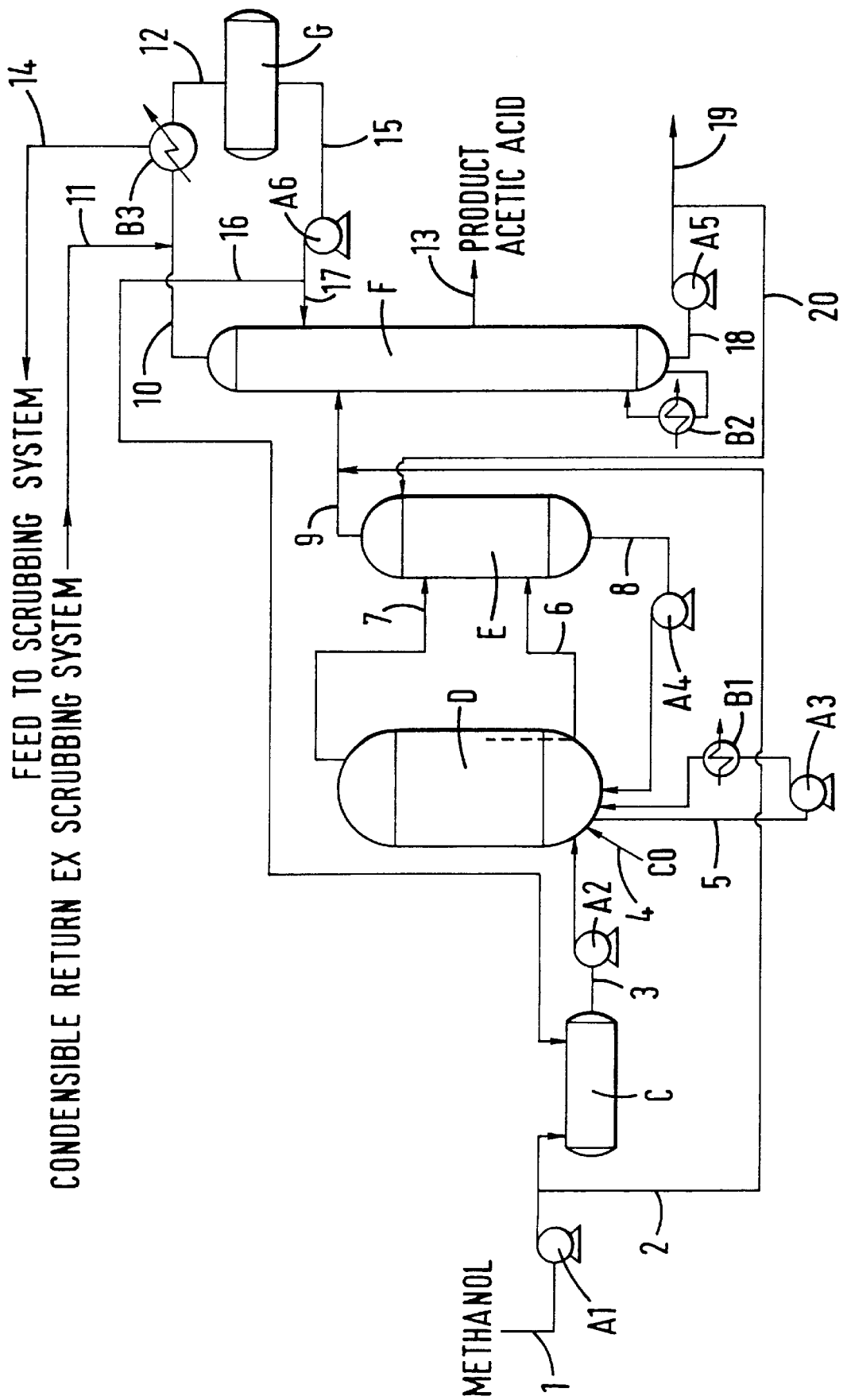

ANHYDROUS CARBONYLATION PROCESS FOR THE PRODUCTION OF ACETIC ACID

The present invention relates to a process for the production of acetic acid by the carbonylation of methanol and/or dimethyl ether in the presence of a Group VIII noble metal carbonylation catalyst.

Acetic acid is a well-known valuable commodity chemical, which is used for example as a preservative and as an intermediate in the production of acetate esters. On an industrial scale acetic acid is produced by the carbonylation of methanol at elevated temperature and pressure in the presence of, for example, a rhodium catalyst and an iodide-containing co-catalyst. In this process the carbonylation of methanol to acetic acid is carried out under steady state conditions by continuously feeding methanol, carbon monoxide, catalyst, iodide co-catalyst and recycled material to a carbonylation reactor whilst at the same time continuously withdrawing an acetic acid-containing product stream. Under typical steady state conditions the carbonylation reaction is carried out in the presence of a standing quantity of 14–15% water to ensure good reaction rates (see, for example, EP-A-55618 and Ind. Eng. Chem. Prod. Res. Dev. 16, 281–285 (1977)). A consequence of such large quantities of water in the reaction mixture is a large 'drying requirement' with associated capital and variable cost penalties. Since the introduction of the Monsanto process effort has been concentrated on, amongst other matters, the development of low water methanol carbonylation technology allowing increased productivity from existing plants and the potential for reduced CAPEX for new plants. Some progress has been made towards this objective. Thus, for example, BP Chemicals' CATIVA (TM) process operates with about 2–8% w/w water in the reactor taking advantage of the reduced loading on existing distillation capacity to increase plant productivity. However, there is still a significant drying requirement. The presence of water in the reaction composition for the production of acetic acid by methanol carbonylation is generally recognised as being necessary, or highly desirable, for maintaining catalyst activity and stability. Nevertheless, reduction or elimination of the water requirement remains a desirable objective.

It is known from, for example GB-A-1468940, that an anhydride of a monocarboxylic acid can be produced by reacting a carboxylate ester satisfying the formula RCOOR or an ether satisfying the formula ROR with an acyl halide satisfying the formula RCOX, formed in situ or in a separate stage, under substantially anhydrous conditions, wherein X is an iodide or bromide, the Rs may be the same or different and each R is a monovalent hydrocarbyl radical or a substituted monovalent hydrocarbon radical wherein the or each substituent is inert. The acyl halide may be produced by carbonylation of a halide satisfying the formula RX at superatmospheric pressure, R and X being as defined hereinabove, and the carbonylation may be effected in the presence as catalyst of a Group VIII noble metal, ie iridium, osmium, platinum, palladium, rhodium and ruthenium, and optionally a promoter selected from elements having atomic weights greater than 5 of Groups IA, IIA, IIIA, IVB, VIB, the non-noble metals of Group VIII and the metals of the lanthanide and actinide groups of the Periodic Table, of which suitable metals are lithium, magnesium, calcium, titanium, chromium, iron, nickel and aluminium. It is stated in GB-A-1468940 that it is important that the carbonylation reaction should be carried out under substantially anhydrous conditions, ie the reactants should be essentially dry.

It is also known to produce acetic anhydride with or without the net co-production of acetic acid. Thus, our EP-A-87870 discloses a process for the production of acetic anhydride with or without the net co-production of acetic acid from methanol and carbon monoxide in a series of esterification, carbonylation and separation steps comprising:

(1) reacting methanol with recycle acetic acid in an esterification step to form an esterification product containing predominantly methyl acetate, water and optionally unreacted methanol, (2) removing part of the water from the esterification product, (3) reacting the esterification product still containing water with carbon monoxide in a carbonylation step in the presence as catalyst of free or combined metallic carbonylation catalyst and as promoter of free or combined halogen to form a carbonylation product containing acetic acid and acetic anhydride, (4) separating the product by fractional distillation into a low-boiling fraction containing carbonylation feed and volatile carbonylation promoter components, acetic acid and acetic anhydride fractions, and a higher-boiling fraction containing carbonylation catalyst components, (5) recycling the low-boiling fraction containing carbonylation feed and carbonylation promoter components and the higher-boiling fraction containing carbonylation catalyst components to the carbonylation step, and (6) recycling at least part of the acetic acid fraction to the esterification step.

This process operates with significant quantities of acetic anhydride in the reactor composition (10–18% w/w) and only produces acetic acid in combination with acetic anhydride.

Processes are known for the production of acetic acid by carbonylation under low water or anhydrous conditions from, for example U.S. Pat. No. 5,281,751; EP-A-0 097978; and EP-A-0 173170.

U.S. Pat. No. 5,281,751 discloses a process for the production of acetic acid by reacting methanol with carbon monoxide in the presence of a rhodium catalyst, methyl iodide, a lithium iodide content of at least about 0.2 moles per liter of reaction medium, the atomic ratio of iodide to lithium being greater than 1, a water content of from 0 to 6.5% by weight and either methyl acetate or a substance convertible thereto, e.g. acids, anhydrides and even esters themselves. Hydrogen is preferably added to the reaction system to maintain a concentration of 1 to 50 mole percent, preferably 2 to 10 mole percent hydrogen.

EP-A-0 097978 discloses a process for the co-production of carboxylic acids of the fomula $R^1CH_2COOH$ and/or $R^2COOH$ and carboxylic acids of the formula $R^1CH_2COOH$ and/or $R^2CH_2COOH$ by reacting one or more compounds of the formula $R^1XR^2$ in which X represents a

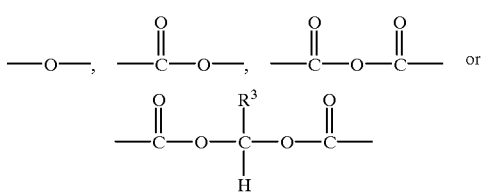

moiety and in which $R^1$, $R^2$ and $R^3$ represent similar or dissimilar alkyl, cycloalkyl, aryl, aralkyl or alkaryl groups, with carbon monoxide and hydrogen in the presence of a rhodium catalyst and an iodide and/or bromide source, characterised in that the reaction is carried out under virtually anhydric conditions and in the presence—per mole of the compound $R^1XR^2$—of at least 2 moles of a carboxylic acid of the formula $R^4COOH$, in which $R^4$ represents an alkyl, cycloalkyl, aryl, aralkyl or alkaryl group. Essentially the process disclosed in EP-A-0 097 978 is a homologation carbonylation, or hydrocarbonylation process, insofar as carbon monoxide and hydrogen are added in more or less equimolar quantities, though the molar ratio between the two compounds may vary within wide limits, for instance in the range 10:1 to 1:10, preferably between 1:0.5 and 1:3.

Finally, EP-A-0 173 170 discloses the production of anhydrous acetic acid and acetic anhydride by the reaction of carbon monoxide and methanol in the presence of a catalyst system containing rhodium as the metal or a compound thereof, a mixture of lithium iodide and methyl iodide, and a specific phosphorus-containing ligand characterised in that the reaction is carried out in the presence of methyl acetate or a compound which under the reaction conditions can be converted to methyl acetate, for example acetic anhydride. The process is characterised by mild reaction conditions, for example temperatures up to 170° C., preferably from 50 to 160° C., more preferably from 105 to 150° C. and pressures up to 31.5 bar, preferably from 7 to 28 bar. No mention is made of hydrogen as a gaseous component and a phosphorous-containing ligand is an essential component of the catalyst.

Whilst it is recognised in the aforesaid disclosures that operation under anhydrous conditions eliminates the need for an expensive water removal step there is no recognition of the fact that the production of substantial amounts of acetic anhydride can lead to the requirement in place thereof of an acetic acid/acetic anhydride separation stage.

There remains a need therefore for an improved process for producing acetic acid at the lowest possible standing water concentration in the reactor.

We have now found that acetic acid can be produced with advantage under anhydrous conditions.

Accordingly the present invention provides an anhydrous process for the production of acetic acid by the reaction of methanol, and/or dimethyl ether, with a gaseous reactant comprising carbon monoxide and hydrogen, the hydrogen being present in an amount less than 9 mole %, in the presence of a catalyst system comprising at least one noble metal of Group VIII of the Periodic Table as catalyst, a halo-compound as co-catalyst and an iodide salt as catalyst stabiliser which process comprises feeding methanol, and/or dimethyl ether, and gaseous reactant to a carbonylation reactor in which there is maintained a liquid reaction composition comprising (i) methyl acetate in an amount from 1 to 35% w/w, (ii) acetic anhydride in an amount up to 8% w/w, (iii) halo-compound in an amount from 3 to 20% w/w, (iv) Group VIII noble metal catalyst in an amount from 1 to 2000 ppm, (v) sufficient iodide salt to provide from 0.5 to 20% by weight iodine as I⁻ (vi) acetic acid comprising the remainder of the composition.

As compared with the process of EP-A-87870 in which much higher standing concentrations of acetic anhydride are present in the reactor the process of the present invention for the production of acetic acid can provide the following principal advantages:

(i) the need for an acetic acid-acetic anhydride separation step can be substantially reduced or eliminated;
(ii) the esterification section can be reduced in size or eliminated;
(iii) carbonylation rates can be increased;
(iv) unwanted polymer make can be significantly reduced or eliminated;

(v) the make rate of non-acidic by-products, for example mesityl oxide, can be reduced; and
(vi) the ethylidene diacetate make rate can be reduced.

As compared with the Monsanto process for the production of acetic acid at high standing water concentrations in the reactor and subsequently developed processes at lower standing water concentrations the anhydrous process of the present invention is advantageous principally in the respect that it eliminates the necessity of a significant water separation step. It can also reduce or eliminate the co-production of by-product carboxylic acids, for example propionic acid.

As feedstock there may be used methanol, dimethyl ether, or methanol in admixture with dimethyl ether, which admixture may suitably be obtained in the manner, for example, of EP-A-566370 or U.S. Pat. No. 5,189,203.

The gaseous reactant comprises carbon monoxide and hydrogen, which may be added separately or in combination. It is possible to use gaseous reactant containing fairly high levels of hydrogen, i.e. up to less than 9 mole %, but this may result in the requirement to employ a further distillation column for the purpose of removing ethylidene diacetate generally formed as by-product in the presence of hydrogen. It is preferred however to operate with as little hydrogen as possible in the gaseous reactant. The amount of hydrogen in the gaseous reactant is suitably such that significant amounts of ethylidene diacetate do not appear in the product. In addition to hydrogen the carbon monoxide may contain carbon dioxide and/or gaseous hydrocarbon, for example methane. Suitably there may be used for example the residual carbon monoxide/hydrogen mixture obtained from the production of methanol/dimethyl ether mixtures as described hereinabove. Suitably the gaseous reactant may contain from 0.01 to 2.5 mole % hydrogen, for example from 0.01 to 1.0 mole % hydrogen, typically about 0.5 mole % hydrogen.

The catalyst system comprises at least one noble metal of Group VIII of the Periodic Table of the Elements. These are defined as osmium, iridium, platinum, palladium, rhodium and ruthenium. Rhodium is a preferred metal and the process will hereinafter be described for the purpose of simplicity with reference to rhodium.

The rhodium component of the catalyst system in the liquid reaction composition may comprise any rhodium-containing compound which is soluble in the liquid reaction composition. The rhodium may be added to the liquid reaction composition in any suitable form which dissolves in the composition or is convertible to a soluble form. Examples of suitable rhodium-containing compounds which may be added to the liquid reaction composition include $[Rh(CO)_2Cl]_2$, $[Rh(CO)_2I]_2$, $[Rh(Cod)Cl]_2$, rhodium (III) chloride, rhodium (III) chloride trihydrate, rhodium (III) bromide, rhodium (III) iodide, rhodium (III) acetate, rhodium dicarbonylacetylacetonate, $RhCl_3$ $(PPh_3)_3$ and $RhCl(CO)(PPh_3)_2$. Rhodium is preferably present in the liquid reaction composition in an amount from 300 to 900 ppm based on the weight of the composition.

The catalyst system further comprises a halo-compound as co-catalyst. A preferred halo-compound is a hydrocarbyl halide, preferably an alkyl halide, which may be added as such or formed in-situ. Suitable alkyl halides are $C_1$ to $C_{10}$, preferably $C_1$ to $C_6$, more preferably $C_1$ to $C_4$ alkyl halides. Of the halides, iodides or bromides are preferred and iodides are more preferred. Preferred as co-catalyst is methyl iodide. The halo-compound is preferably present in the liquid reaction composition in an amount from 8 to 18% by weight based on the weight of the composition.

The catalyst system may further comprise as promoter at least one of the metals ruthenium, osmium, cadmium, mercury and zinc in free or combined form. A preferred promoter is ruthenium, which may be added in any suitable form which dissolves in the reaction composition, such as for example a salt or complex of ruthenium II, III or IV. Typically the molar ratio of promoter relative to rhodium may be in the range 0.1:1 to 10:1.

The catalyst system further comprises an iodide salt as a catalyst stabiliser. Such an iodide salt can be any metal iodide, quaternary ammonium iodide or quaternary phosphonium iodide salt. Preferably, the metal iodide is an alkali metal iodide or alkaline earth metal iodide, more preferably an iodide of lithium, sodium, potassium or cesium, even more preferably lithium iodide. Suitable quaternary ammonium iodides include quaternised amine, pyridine, pyrrolidine or imidazole for example N, N'-dimethyl imidazolium iodide. Suitable quaternary phosphonium iodides include methyl tributyl phosphonium iodide, tetrabutyl phosphonium iodide, methyl triphenyl phosphonium iodide, and the like. Such iodide salt stabilisers are described for example in EP-A-0573189. The amounts of iodide salts employed are sufficient to provide from 0.5 to 20% by weight iodine as $I^{31}$.

A typical catalyst system comprises rhodium and lithium, and possibly also ruthenium as promoter.

The liquid reaction composition comprises (i) methyl acetate, which may be formed in situ by an esterification reaction of methanol reactant with acetic acid product. Methyl acetate may also be returned to the reactor in one or more recycle streams. It may be necessary to add methyl acetate to the liquid reaction composition in the reactor to compensate for any removed therefrom. Methyl acetate is preferably present in the liquid reaction composition in an amount from 5 to 25% w/w.

The liquid reaction composition also comprises (ii) acetic anhydride in an amount up to 8% w/w, preferably up to 5% w/w, more preferably from greater than 0.1 to 3.0% w/w. A standing concentration of acetic anhydride in the liquid reaction composition maintains the composition anhydrous. Acetic anhydride may be formed by the carbonylation of methyl acetate in the composition, or possibly, for example by the reaction of acyl iodide (formed in situ) with methyl acetate.

In addition to (i) and (ii) the liquid reaction composition further comprises (iii) halo-compound and (iv) Group VIII noble metal, and preferably also an iodide salt as a catalyst stabiliser the remainder of the composition comprising (v) acetic acid.

The process of the invention may be operated as a batch or continuous process, preferably as a continuous process.

Acetic acid essentially free of acetic anhydride is recovered as the product of the process, and there is no simultaneous recovery of acetic anhydride.

In a preferred embodiment the present invention provides an anhydrous process for the production of acetic acid which process comprises the steps of:

(1) feeding methanol, and/or dimethyl ether, and gaseous reactant comprising carbon monoxide and hydrogen in an amount up to 0.5 mole % to a carbonylation reactor at elevated temperature and pressure, there being maintained in the reactor a liquid reaction composition comprising (i) methyl acetate in an amount from 12 to 21% w/w, (ii) acetic anhydride in an amount up to 3% w/w, (iii) halo-compound co-catalyst in an amount from 9 to 16% w/w, (iv) Group VIII noble metal catalyst in an amount from 500 to 800 ppm and (v) an iodide salt or salts in an amount in the range from 7 to 14% w/w, (vi) ruthenium promoter in a molar ratio relative to rhodium in the range from 0.1:1 to 5:1 and (vii) acetic acid comprising the remainder of the liquid reaction composition, (2) recovering substantially pure acetic acid from the liquid reaction composition by withdrawing liquid reaction composition from the reactor and separating acetic acid in the withdrawn composition by one or more flash and/or fractional distillation stages from the other components of the composition, and (3) recycling the other components separated from the acetic acid to the carbonylation reactor.

In a more preferred embodiment the present invention comprises an anhydrous process for the production of acetic acid which process comprises the steps of:

(a) feeding methanol and gaseous reactant comprising carbon monoxide and hydrogen in an amount up to 0.5 mole % to a carbonylation reactor held at elevated temperature and pressure, there being maintained in the reactor a liquid reaction composition comprising (i) methyl acetate in an amount from 12 to 21% w/w, (ii) acetic anhydride in an amount up to 3% w/w, (iii) methyl iodide co-catalyst in an amount from 9 to 16% w/w, (iv) rhodium catalyst in an amount from 500 to 800 ppm and (v) an iodide salt or salts in an amount in the range from 7 to 14% w/w, (vi) ruthenium promoter in a molar ratio relative to rhodium in the range from 1:1 to 5:1 and (vii) acetic acid comprising the remainder of the liquid reaction composition, (b) withdrawing liquid reaction composition from the reactor and passing the composition to a flash separation zone at a total pressure less than that of the carbonylation reactor, wherein with or without the addition of heat, vapour and liquid fractions are formed from the liquid reaction composition, the vapour fraction comprising acetic acid, methyl iodide, small amounts of acetic anhydride, methyl acetate, and possibly also higher- and lower-boiling impurities, and the liquid fraction comprising acetic acid, acetic anhydride, rhodium catalyst, ruthenium promoter, iodide salt(s) and possibly also some methyl acetate and/or methyl iodide and/or higher boiling impurities, (c) recycling all or part of the liquid fraction to the carbonylation reactor, (d) feeding all or part of the vapour fraction to an intermediate point in a fractional distillation column from which there is removed from the base a fraction comprising acetic acid, any acetic anhydride and any higher-boiling impurities, there is removed overhead a vapour fraction comprising methyl iodide, methyl acetate, methanol and any lower-boiling impurities and there is removed intermediate the base and the top of the column a product fraction comprising substantially pure acetic acid, and (e) recycling all or part of the overhead fraction from the fractional distillation column to the carbonylation reactor.

The carbonylation reactor is suitably held at a temperature in the range from 150 to 210, preferably from 170 to 195° C., for example from greater than 170 to 195° C., and a pressure in the range from 10 to 100, preferably from 20 to 40 bar.

In addition to the rhodium catalyst and the methyl iodide co-catalyst, the carbonylation reactor preferably also contains a metal promoter, for example ruthenium, and a catalyst stabiliser in the form of one or more iodide salts, for example lithium iodide and QAS.

In step (b) of the process liquid reaction composition is passed to a flash separation zone at a total pressure less than that of the carbonylation reactor. Suitably the pressure in the flash separation zone is from 0.5 to 5 bar.

To ease the separation of acetic anhydride from acetic acid in the liquid reaction composition it is preferred to convert as much as possible of the acetic anhydride by reaction with added methanol to methyl acetate. The methanol is suitably added for this purpose at a point such that the conversion of acetic anhydride to methyl acetate is maximised, which may be to the flash separation zone or to the fractional distillation column, preferably the latter. In this manner acetic anhydride is effectively separated and recycled to the carbonylation reactor in the form of the more easily separable methyl acetate. Furthermore, the need for an esterification section is reduced or eliminated.

In step (c) of the process all or part of the liquid fraction separated in the flash separation zone is recycled to the carbonylation reactor. It may be desirable from time to time to remove a portion of the liquid fraction for the purpose of removing accumulated polymer and/or other unwanted by-products therefrom before returning the portion of the liquid fraction to the carbonylation reactor. The polymer so-obtained may be disposed of after recovery therefrom of any rhodium catalyst and/or metal promoter residues.

In step (d) of the process all or part of the vapour fraction separated in the flash distillation zone is fed to an intermediate point in a fractional distillation column. That part of the vapour fraction not fed to the flash distillation zone may suitably be recycled to the carbonylation reactor, The vapour fraction removed overhead from the fractional distillation column may suitably be condensed, part of the condensate being returned to the fractional distillation column as reflux and the remainder being returned to the carbonylation reactor. From the base of the fractional distillation column there is removed a fraction comprising acetic acid, any acetic anhydride and high-boiling impurities, typically ethylidene diacetate. It is preferred to recover acetic acid from this fraction. Intermediate the base and the top of the column there is removed a product fraction comprising substantially pure acetic acid, which may or may not be further purified.

A preferred embodiment of the present invention will now be described with reference to the accompanying FIGURE which is a process flow diagram.

With reference to the FIGURE the items designated A are pumps, the items designated B are heat exchangers, the items designated 1–20 are material transfer lines, C is a pre-mixing holding tank, D is a carbonylation reactor, E is a flashtank, F is a fractional distillation column, and G is a liquid distillate tank.

In operation methanol is fed via the pump A1 to the holding tank C and then via line 3 and the pump A2 to the carbonylation reactor D. Also fed to the carbonylation reactor D is carbon monoxide and hydrogen. Exothermic heat of reaction is removed by pumping via line 5 and pump A3 liquid reaction composition through heat exchanger B1 before returning it to the reactor D. The reactor is maintained at a temperature typically in the range from about 170 to 200° C. for example 180 to 195° C. and a total pressure typically of between 25 and 40 barg, for example about 36 barg.

The liquid reaction composition in the reactor D typically comprises:

acetic anhydride: 2% w/w
methyl acetate: 12–21% w/w, for example 20% w/w
methyl iodide: 13.5–14.5% w/w, for example 14% w/w
rhodium: 550–750 ppm, for example 700 ppm
ionic iodide (e.g. lithium): 10.0–12.5% w/w, for example 16% w/w ruthenium: about 5:1 molar relative to rhodium.

From the reactor D through line 6 liquid reaction composition is fed to the flash tank E at a pressure of 1.5 to 2.5 bar. Overhead from the reactor D through line 7 as a continuous purge may be taken high pressure off-gas (HPOG) containing gaseous inerts and possibly also one or more of methyl iodide, methyl acetate, acetic acid and acetic anhydride, which is also fed to the flash tank E. In the flash tank a separation occurs between a liquid fraction comprising acetic acid, rhodium catalyst and any metal promoters and/or stabilisers and a vapour fraction comprising acetic acid, methyl iodide, acetic anhydride, methyl acetate, high- and lower-boilers and permanent gases. The liquid fraction is returned via pump A4 and line 8 to the carbonylation reactor D. The vapour fraction is fed via line 9 to the fractional distillation column F, which has an overhead take-off through line 10, a base take-off through line 18, a side take-off through line 13, and a reboiler B2. The column typically has 20 theoretical stages (inclusive of reboiler but not overhead condenser) with the side tale-off being situated at stage 16. A portion of the methanol fed through line I is taken through line 2 after pump A1 and is fed through line 9 to the fractional distillation column F; it reacts both in line 9 and in the fractional distillation column with any acetic anhydride in the vapour fraction taken from the flash tank E to convert it to methyl acetate.

A portion of the base take-off from column F is recycled via line 20 and pump A5 to the flash tank E as wash therefor. The remaining portion is removed from the plant for further treatment if desired.

The side take off comprising product acetic acid is taken from the column F through line 13 and passed to a product holding tank. It is an advantage of the process of the invention that the product acetic acid does not require any treatment to bring it within the permanganate time specification. It may however be desirable to further purify it by removal of other impurities, for example ethylidene diacetate.

The vapour take-off removed through line 10 is condensed in heat exchanger B3, the condensate comprising methyl acetate, methyl iodide, methanol and acetic acid being passed through line 12 to the liquid distillate tank G, from which part is returned to tank C through line 16, and part is returned as reflux via pump A6 and line 17 to column F.

The vapour stream from the top of the overheads condenser B4 is fed to a scrubbing system for further treatment through line 18. Any recovered material is returned from the scrubbing system through line 11.

The invention will now be illustrated by reference to the following Examples. In the Examples the method described hereinabove with reference to the FIGURE was employed except that instead of a side take-off through line 13 a fraction was taken through line 18 from the base of the distillation column F.

EXAMPLES 1 TO 3 AND COMPARISON TEST 1

In these Examples methanol was not fed to either the flash tank E or the distillation column F.

The liquid reaction composition and the carbon monoxide feed rate are given in Table 1. In the Examples acetic acid was the major product. The gaseous and liquid products other than acetic acid are given in Table 2. Comparison Test 1 is not an example according to the present invention because of the high acetic anhydride concentration in the liquid reaction composition. It is included only for the purpose of comparison.

EXAMPLE 4

The effect of feeding methanol to the flash tank E is shown in Table 3.

TABLE 1

|  | Example | | | |
|---|---|---|---|---|
|  | 1 | 2 | 3 | Comp. Test 1 |
| Liquid reaction composition | | | | |
| Acetic anhydride (% w/w) | 2 | 2 | 2 | |
| Methyl acetate (% w/w) | 19 | 13 | 21 | 20 |
| Rh (ppm) | 640 | 700 | 480 | 750 |
| Li (ppm) | 5340 | 5300 | 9000 | 5600 |
| Gas | | | | |
| Carbon monoxide rate mol/lh | 8 | 8.2 | 7.5 | 8 |
| Reactor conditions | | | | |
| Temperature (° C.) | 179 | 177 | 189 | 184 |

TABLE 2

|  | Example | | | |
|---|---|---|---|---|
|  | 1 | 2 | 3 | Comp. Test 1 |
| Gaseous product make | | | | |
| Carbon dioxide (mmol/lh) | 0.2 | 0.17 | 2.0 | 3.1 |
| Polymer (tepa) | 0* | 0* | 0* | 70 |
| Liquid product make | | | | |
| Other key acetone derived by-products (ppm) | 11 | 11 | 21 | 98 |
| Ethylidene diacetate (ppm) | 500 | 680 | 200 | 1125 |

*Undetectable

TABLE 3

| Methanol feed to: | None | Flash Tank E |
|---|---|---|
| Methanol feed (ml/h) | 0 | 1000 |
| Acetic anhydride (% w/w) - distillation column F base take-off | 7.4 | 1.3 |
| Acetic anhydride (% w/w) - carbonlation reactor D | 2.7 | 2.1 |
| Distillation column F base take-off rate (kg/h) | 9.8 | 9.4 |
| Carbon monoxide rate (mol/lh) | 8.99 | 9.9 |
| Methanol conversion (%) | — | 19 |

What is claimed is:

1. An anhydrous continuous process for the production of acetic acid as the major product without simultaneous recovery of acetic anhydride by the reaction in a carbonylation reactor of methanol with a gaseous reactant comprising carbon monoxide and hydrogen, the hydrogen being present in an amount less than 9 mole %, in the presence of a catalyst system comprising at least one noble metal of Group VIII of the Periodic Table as catalyst, a halo-compound as co-catalyst and an iodide salt as catalyst stabiliser which process comprising feeding methanol and gaseous reactant to a carbonylation reactor in which there is maintained a liquid reaction composition comprising (i) methyl acetate in an amount from 1 to 35% w/w, (ii) acetic anhydride in an amount up to 8% w/w, (iii) halo-compound in an amount from 3 to 20% w/w, (iv) Group VIII noble metal catalyst in an amount from 1 to 2000 ppm, (v) sufficient iodide salt to provide from 0.5 to 20% by weight iodine as I$^-$ and (vi) acetic acid.

2. A process according to claim 1 wherein the gaseous reactant contains from 0.01 to 2.5 mole % hydrogen.

3. A process according to claim 2 wherein the gaseous reactant contains from 0.01 to 1.0 mole % hydrogen.

4. A process according to claim 1 wherein the noble metal of Group VIII of the Periodic Table is rhodium.

5. A process according to claim 1 wherein the co-catalyst is methyl iodide.

6. A process according to claim 5 wherein the methyl iodide is present in the liquid reaction composition in an amount from 8 to 18% by weight based on the weight of the composition.

7. A process according to claim 1 wherein the catalyst system further comprises ruthenium as promoter.

8. A process according to claim 1 wherein the catalyst stabiliser is an alkali metal or alkaline earth metal iodide.

9. A process according to claim 8 wherein the catalyst stabiliser is an iodide of lithium, sodium, potassium or cesium.

10. A process according to claim 1 wherein the amount of iodide salt employed is sufficient to provide from 0.5 to 20% by weight iodine as I$^-$.

11. A process according to claim 1 wherein methyl acetate is present in the liquid reaction composition in an amount from 5 to 25% w/w.

12. A process according to claim 1 wherein the liquid reaction composition comprises acetic anhydride in an amount up to 5% w/w.

13. A process according to claim 1 wherein the liquid reaction composition comprises acetic anhydride in an amount from greater than 0.1 to 3.0% w/w.

14. An anhydrous continuous process for the production of acetic acid as the major product without simultaneous recovery of acetic anhydride by the reaction of methanol with a gaseous reactant comprising carbon monoxide and hydrogen which comprises the steps of:

(1) feeding methanol and gaseous reactant comprising carbon monoxide and hydrogen in an amount up to 0.5 mole % to a carbonylation reactor at elevated temperature and pressure, there being maintained in the reactor a liquid reaction composition comprising (i) methyl acetate in an amount from 12 to 21% w/w, (ii) acetic anhydride in an amount up to 3% w/w, (iii) halo-compound co-catalyst in an amount from 9 to 16% w/w, (iv) a rhodium catalyst in an amount from 500 to 800 ppm and (v) an iodide salt or salts in an amount in the range from 7 to 14% w/w, (vi) ruthenium promoter in a molar ratio relative to rhodium in the range from 0.1:1 to 5:1 and (vii) acetic acid, (2) recovering substantially pure acetic acid from the liquid reaction composition by withdrawing liquid reaction composition from the reactor and separating acetic acid in the withdrawn composition by one or more flash and/or fractional distillation stages from the other components of the composition, and (3) recycling the other components separated from the acetic acid to the carbonylation reactor.

15. An anhydrous continuous process for the production of acetic acid as the major product without simultaneous recovery of acetic anhydride by the reaction of methanol with a gaseous reactant comprising carbon monoxide and hydrogen which process comprises the steps of:

(a) feeding methanol and gaseous reactant comprising carbon monoxide and hydrogen in an amount up to 0.5% mole % to a carbonylation reactor held at elevated temperature and pressure, there being maintained in the reactor a liquid reaction composition comprising (i) methyl acetate in an amount from 12 to 21% w/w, (ii) acetic anhydride in an amount up to 3% w/w, (iii) methyl iodide co-catalyst in an amount from 9 to 16% w/w, (iv) rhodium catalyst in an amount from 500 to 800 ppm and (v) an iodide salt or salts in an amount in the range from 7 to 14% w/w, (vi) ruthenium promoter in a molar ratio relative to rhodium in the range from 1:1 to 5:1 and (vii) acetic acid, (b) withdrawing liquid reaction composition from the reactor and passing the composition to a flash separation zone at a total pressure less than that of the carbonylation reactor, wherein with or without the addition of heat, vapor and liquid fractions are formed from the liquid reaction composition, the vapor fraction comprising acetic acid, methyl iodide, small amounts of acetic anhydride, methyl acetate; and possibly also higher-and lower-boiling impurities, and the liquid fraction comprising acetic acid, acetic anhydride, rhodium catalyst, ruthenium promoter, iodide salt(s) and possibly also some methyl acetate and/or methyl iodide and/or higher boiling impurities.

(c) recycling all or part of the liquid fraction to the carbonylation reactor, (d) feeding all or part of the vapor fraction to an intermediate point in a fractional distillation column from which there is removed from the base a fraction comprising acetic acid, any acetic anhydride and any higher-boiling impurities, there is removed overhead a vapor fraction comprising methyl iodide, methyl acetate, methanol and any lower-boiling impurities and there is removed intermediate the base and the top of the column a product fraction comprising substantially pure acetic acid, and (e) recycling all or part of the overhead fraction from the fractional distillation column to the carbonylation reactor.

16. A process according to claim 15 wherein methanol is added either to the flash separation zone or to the fractional distillation column wherein it is reacted with acetic anhydride to convert as much as possible thereof to methyl acetate.

17. A process according to claim 1 wherein the carbonylation reactor is held at a temperature in the range from 150 to 210° C.

18. A process according to claim 17 wherein the temperature is in the range from greater than 170 to 195° C.

19. A process according to claim 1 wherein the carbonylation reactor is held at a pressure in the range from 20 to 40 bar.

20. A process according to claim 15 wherein methanol is added either to the flash separation zone or to the fractional distillation column wherein it is reacted with acetic anhydride to convert as much as possible thereof to methyl acetate.

21. A process according to claim 1 and further comprising feeding methanol and dimethyl ether to said carbonylation reaction.

22. A process according to claim 15 and further comprising feeding methanol and dimethyl ether to said carbonylation reaction.

23. A process according to claim 1 wherein the Group VIII metal is rhodium, the halo compound is methyl iodide and the iodide salt catalyst stabilizer is an alkali metal iodide or an alkaline earth metal iodide.

24. A process according to claim 14 wherein the Group VIII metal is rhodium, the halo compound is methyl iodide and the iodide salt catalyst stabilizer is an alkali metal iodide or an alkaline earth metal iodide.

* * * * *